(12) United States Patent
Reevell

(10) Patent No.: US 10,939,704 B2
(45) Date of Patent: Mar. 9, 2021

(54) AEROSOL-GENERATING ARTICLE WITH CAPACITOR

(71) Applicant: Philip Morris Products S.A., Neuchatel (CH)

(72) Inventor: Tony Reevell, London (GB)

(73) Assignee: Philip Morris Products S.A., Neuchatel (CH)

( * ) Notice: Subject to any disclaimer, the term of this patent is extended or adjusted under 35 U.S.C. 154(b) by 339 days.

(21) Appl. No.: 15/759,413

(22) PCT Filed: Sep. 23, 2016

(86) PCT No.: PCT/EP2016/072771
§ 371 (c)(1),
(2) Date: Mar. 12, 2018

(87) PCT Pub. No.: WO2017/051016
PCT Pub. Date: Mar. 30, 2017

(65) Prior Publication Data
US 2018/0206553 A1    Jul. 26, 2018

(30) Foreign Application Priority Data

Sep. 24, 2015 (EP) .................................... 15186772

(51) Int. Cl.
*A24F 13/00* (2006.01)
*A24F 47/00* (2020.01)
*A61M 15/06* (2006.01)

(52) U.S. Cl.
CPC .......... *A24F 47/008* (2013.01); *A61M 15/06* (2013.01)

(58) Field of Classification Search
CPC ....................................................... A24F 47/00

USPC .................................................. 131/328–329
See application file for complete search history.

(56) References Cited

U.S. PATENT DOCUMENTS

| 3,860,012 A | 1/1975 | Selke |
| 3,894,544 A | 7/1975 | Egri |
| 5,498,855 A | 3/1996 | Deevi et al. |
| 5,514,630 A | 5/1996 | Willkens et al. |

(Continued)

FOREIGN PATENT DOCUMENTS

| CN | 1330563 A | 1/2002 |
| CN | 103404969 A | 11/2013 |

(Continued)

OTHER PUBLICATIONS

Office Action dated Sep. 26, 2019 in corresponding Russian Patent Application No. 2018114886 (with English Translation), citing documents AA and AO therein 18 pages.

(Continued)

*Primary Examiner* — Phuong K Dinh
(74) *Attorney, Agent, or Firm* — Oblon, McClelland, Maier & Neustadt, L.L.P.

(57) ABSTRACT

An aerosol-generating article is provided, including an aerosol-generating substrate including tobacco; and a capacitor including a first electrode, a second electrode, and a dielectric material disposed between the first electrode and the second electrode, the dielectric material including a porous substrate material and a liquid sorbed into the porous substrate material. There is also provided an aerosol-generating system including the aerosol-generating article in combination with an aerosol-generating device.

14 Claims, 6 Drawing Sheets

(56) References Cited

U.S. PATENT DOCUMENTS

| | | | |
|---|---|---|---|
| 5,724,998 | A | 3/1998 | Gellatly et al. |
| 5,996,903 | A | 12/1999 | Asai et al. |
| 2013/0220315 | A1 | 8/2013 | Conley et al. |
| 2014/0096781 | A1 | 4/2014 | Sears et al. |
| 2014/0290677 | A1 | 10/2014 | Liu |
| 2015/0366266 | A1 | 12/2015 | Chen |
| 2016/0157523 | A1 | 6/2016 | Liu |
| 2016/0302488 | A1 | 10/2016 | Fernando et al. |
| 2018/0146715 | A1* | 5/2018 | Takeuchi ............... A61M 15/06 |
| 2019/0289916 | A1* | 9/2019 | Bowen ................. H05B 1/0244 |

FOREIGN PATENT DOCUMENTS

| | | |
|---|---|---|
| CN | 104106844 A | 10/2014 |
| EP | 2 489 391 A1 | 8/2012 |
| GB | 983928 A | 2/1965 |
| GB | 2476005 A | 6/2011 |
| JP | 2014-217379 A | 11/2014 |
| JP | 2015-506170 A | 3/2015 |
| WO | WO 03/095688 A2 | 11/2003 |
| WO | WO 2011/160788 A1 | 12/2011 |
| WO | 2015/015431 A1 | 2/2015 |
| WO | 2015/082560 A1 | 6/2015 |
| WO | 2015/151053 A2 | 10/2015 |

OTHER PUBLICATIONS

Combined Chinese Office Action and Search Report dated May 28, 2020 in Chinese Patent Application No. 201680051651.0 (with English translation), citing documents AA and AO through AR therein, 16 pages.

International Search Report and Written Opinion dated Jan. 23, 2017 in PCT/EP2016/072771 filed Sep. 23, 2016.

Japanese Notification of Reasons for Refusal dated Oct. 19, 2020 in corresponding Japanese Patent Application No. 2018-513313 (with English translation), 5 pages.

* cited by examiner

AEROSOL-GENERATING ARTICLE WITH CAPACITOR

TECHNICAL FIELD

The present invention relates to an aerosol-generating article comprising a capacitor, and an aerosol-generating system comprising the aerosol-generating article.

DESCRIPTION OF THE RELATED ART

One type of aerosol-generating system is an electrically operated smoking system. Known handheld electrically operated smoking systems typically comprise an aerosol-generating device comprising a battery, control electronics and an electric heater for heating an aerosol-generating article designed specifically for use with the aerosol-generating device. In some examples, the aerosol-generating article comprises an aerosol-generating substrate, such as a tobacco rod or a tobacco plug, and the heater contained within the aerosol-generating device is inserted into or around the aerosol-generating substrate when the aerosol-generating article is inserted into the aerosol-generating device. In an alternative electrically operated smoking system, the aerosol-generating article may comprise a capsule containing an aerosol-generating substrate, such as loose tobacco.

Aerosol-generating substrates, such as tobacco, typically comprise one or more volatile compounds that form an aerosol when heated inside the aerosol-generating device. During continuous heating inside an aerosol-generating device the volatile compounds are depleted from the aerosol-generating substrate until the level of volatile compounds remaining within the aerosol-generating substrate may be insufficient to support adequate aerosol generation, which may lead to a diminished smoking experience for a consumer.

Accordingly, it would be desirable to provide an aerosol-generating article that enables monitoring of the levels of volatile compounds remaining in an aerosol-generating substrate during heating of the aerosol-generating substrate.

SUMMARY

According to a first aspect of the present invention there is provided an aerosol-generating article comprising an aerosol-generating substrate and a capacitor. The aerosol-generating substrate comprises tobacco. The capacitor comprises a first electrode, a second electrode, and a dielectric material positioned between the first electrode and the second electrode. The dielectric material comprises a porous substrate material and a liquid sorbed into the porous substrate material.

BRIEF DESCRIPTION OF THE DRAWINGS

Embodiments of the invention will now be described, by way of example only, with reference to the accompanying drawings, in which.

DETAILED DESCRIPTION

Figure 1:
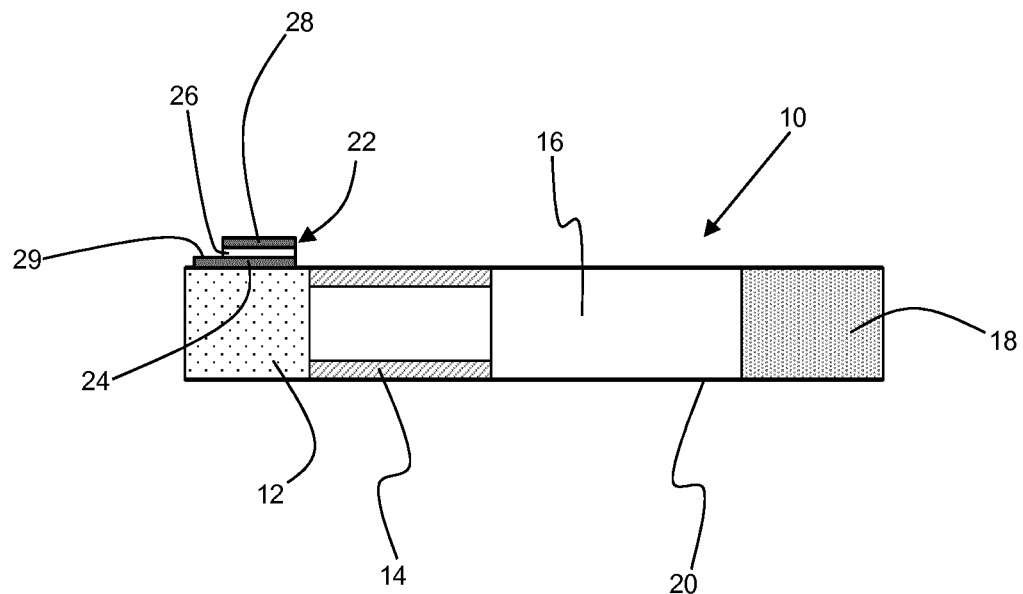
FIG. 1 shows an aerosol-generating article in accordance with the present invention.

As used herein, the term "aerosol-generating article" refers to an article comprising an aerosol-generating substrate that, when heated, releases volatile compounds that can form an aerosol. Preferably, the aerosol-generating substrate is non-liquid at room temperature, where room temperature is 20 degrees Celsius.

Aerosol-generating articles according to the present invention advantageously comprise a capacitor in which the dielectric material comprises a porous substrate material and a liquid sorbed into the porous substrate material. Advantageously, when the aerosol-generating article is heated during use, for example in an aerosol-generating device, the liquid sorbed into the porous substrate material evaporates. Evaporation of the liquid from the dielectric material results in a change in the permittivity of the dielectric material, which in turn results in a change in the capacitance between the first electrode and the second electrode. The change in capacitance between the first electrode and the second electrode can advantageously be used to give an indication of the amount of one or more volatile compounds remaining in the aerosol-generating substrate.

As discussed in more detail below, the dielectric material may be separate from the aerosol-generating substrate. In such embodiments, measuring the change in capacitance between the first electrode and the second electrode may provide an indirect measurement of the amount of one or more volatile compounds remaining in the aerosol-generating substrate based on a known correlation between the rate of loss of liquid from the dielectric material and the rate of loss of volatile compounds from the aerosol-generating substrate when the aerosol-generating article is heated using a known aerosol-generating device.

Alternatively, as discussed in more detail below, at least part of the aerosol-generating substrate may form the dielectric material. In such embodiments, measuring the change in capacitance between the first electrode and the second electrode may provide a more direct measurement of the amount of one or more volatile compounds remaining in the aerosol-generating substrate.

Using a capacitor to monitor the amount of one or more volatile compounds remaining in the aerosol-generating substrate advantageously facilitates the use of a heating cycle of length appropriate to the aerosol-generating substrate. For example, an aerosol-generating device may be configured to cease heating of the aerosol-generating article when the capacitance, or a change in capacitance, reaches a predetermined threshold indicative of a substantial depletion of the one or more volatile compounds from the aerosol-generating substrate. Preventing further heating of the aerosol-generating article when the one or more volatile compounds have been depleted from the aerosol-generating substrate may prevent the onset of a diminished smoking experience for a consumer. Preventing further heating of the aerosol-generating article when the one or more volatile compounds have been depleted from the aerosol-generating substrate may reduce the risk of accidental combustion of the aerosol-generating substrate due to overheating as the aerosol-generating substrate becomes dry.

The aerosol-generating article may comprise a wrapper wrapped around the aerosol-generating substrate, wherein the capacitor is provided on an outer surface of the wrapper. Providing the capacitor on an outer surface of a wrapper may facilitate the addition of a capacitor to existing aerosol-generating articles with minimal modification to existing high speed manufacturing machines and processes. For example, in some embodiments the aerosol-generating substrate may comprise a tobacco plug or a tobacco rod and the wrapper may comprise a cigarette paper wrapper around the tobacco. In such embodiments, the capacitor may be preformed in an offline process and subsequently secured to an outer surface of the wrapper in a final stage of the manufacture of the aerosol-generating article. Alternatively, the first electrode, the dielectric material and the second electrode can be separately provided and secured to the aerosol-generating article so that the capacitor is formed in situ on the wrapper.

Preferably, the first electrode overlies at least a portion of the wrapper, wherein the dielectric material overlies a first portion of the first electrode, wherein the second electrode overlies at least a portion of the dielectric material, and wherein the first electrode comprises a second portion that does not underlie either the dielectric material or the second electrode. Providing the first electrode with a second portion that does not underlie either the dielectric material or the second electrode may facilitate connection of the first electrode to a corresponding electrical contact of an aerosol-generating device when the aerosol-generating article is combined with the aerosol-generating device to form an aerosol-generating system.

As used herein, the terms 'inner', 'outer', 'underlie' and 'overlie' are used to refer to relative positions of components of the aerosol-generating article, or parts of components of the aerosol-generating article. For example, an inner surface of a component faces toward an interior of the article and an outer surface of a component faces toward the exterior of the article. Similarly, in an example in which a first component underlies a second component, the first component is positioned closer to the interior of the article than the second component. In such an example, the second component overlies the first component.

Alternatively, the aerosol-generating article may comprise a wrapper wrapped around the aerosol-generating substrate, wherein the first electrode underlies at least a portion of the wrapper, wherein the second electrode overlies at least a portion of the wrapper, and wherein the portion of the wrapper positioned between the first electrode and the second electrode forms the dielectric material. In such embodiments, using at least a portion of the wrapper to form the dielectric material eliminates the need to provide a separate dielectric material to form the capacitor.

The wrapper may be formed from a cellulosic material, such as a paper. For example, the wrapper may be a cigarette paper. In these embodiments, the solid components of the cellulosic material form the porous substrate material. The liquid sorbed into the porous substrate material may comprise the residual moisture content of the cellulosic material after the wrapper has been formed using a conventional paper-making process, such as a wet-laying process. Additionally, or alternatively, a liquid may be added to the paper after the paper has been formed. The liquid may comprise water.

In a further alternative, the aerosol-generating article may comprise a wrapper wrapped around the aerosol-generating substrate, wherein the capacitor is positioned between the wrapper and the aerosol-generating substrate. Positioning the capacitor between the wrapper and the aerosol-generating substrate may protect the capacitor from damage during post-manufacture handling of the aerosol-generating article.

To facilitate connection of the first and second electrodes to corresponding electrical contacts on an aerosol-generating device, preferably at least a portion of each of the first and second electrodes is exposed. For example, the wrapper may comprise at least one aperture through which at least a portion of the first and second electrodes can be contacted by corresponding electrical contacts on an aerosol-generating device.

In any of the embodiments described above, the aerosol-generating substrate may have a substantially cylindrical shape, wherein the capacitor has a substantially annular shape and circumscribes at least a portion of the aerosol-generating substrate. Providing a capacitor having a substantially annular shape may advantageously eliminate the need to maintain a specific rotational orientation of the aerosol-generating article upon insertion into an aerosol-generating device. That is, an annular capacitor may facilitate connection of the first and second electrodes to corresponding electrical contacts on an aerosol-generating device in any rotational orientation of the aerosol-generating article.

In a yet further alternative set of embodiments, at least a portion of the aerosol-generating substrate may be positioned between the first electrode and the second electrode so that the portion of the aerosol-generating substrate positioned between the first electrode and the second electrode forms the dielectric material. Such embodiments advantageously eliminate the need to provide a separate dielectric material. Such embodiments advantageously facilitate a more direct measurement of the depletion of volatile compounds from the aerosol-generating substrate by measuring the change in capacitance between the first electrode and the second electrode.

In any of the embodiments described above, the aerosol-generating substrate is preferably a solid aerosol-generating substrate. The aerosol-generating substrate preferably comprises a tobacco-containing material containing volatile tobacco flavour compounds which are released from the substrate upon heating. The aerosol-generating substrate may comprise tobacco-containing material and non-tobacco containing material.

The solid aerosol-generating substrate may comprise, for example, one or more of: powder, granules, pellets, shreds, strands, strips or sheets containing one or more of: herb leaf, tobacco leaf, tobacco ribs, expanded tobacco and homogenised tobacco.

Optionally, the solid aerosol-generating substrate may contain tobacco or non-tobacco volatile flavour compounds, which are released upon heating of the solid aerosol-generating substrate. The solid aerosol-generating substrate may also contain one or more capsules that, for example, include additional tobacco volatile flavour compounds or non-tobacco volatile flavour compounds and such capsules may melt during heating of the solid aerosol-generating substrate.

Optionally, the solid aerosol-generating substrate may be provided on or embedded in a thermally stable carrier. The carrier may take the form of powder, granules, pellets, shreds, strands, strips or sheets. The solid aerosol-generating substrate may be deposited on the surface of the carrier in the form of, for example, a sheet, foam, gel or slurry. The solid aerosol-generating substrate may be deposited on the entire surface of the carrier, or alternatively, may be deposited in a pattern in order to provide a non-uniform flavour delivery during use.

As used herein, the term 'homogenised tobacco material' denotes a material formed by agglomerating particulate tobacco.

As used herein, the term 'sheet' denotes a laminar element having a width and length substantially greater than the thickness thereof.

As used herein, the term 'gathered' is used to describe a sheet that is convoluted, folded, or otherwise compressed or constricted substantially transversely to a longitudinal axis of the aerosol-generating article.

In a preferred embodiment, the aerosol-generating substrate comprises a gathered textured sheet of homogenised tobacco material.

As used herein, the term 'textured sheet' denotes a sheet that has been crimped, embossed, debossed, perforated or otherwise deformed. The aerosol-generating substrate may comprise a gathered textured sheet of homogenised tobacco material comprising a plurality of spaced-apart indentations, protrusions, perforations or a combination thereof.

In a particularly preferred embodiment, the aerosol-generating substrate comprises a gathered crimped sheet of homogenised tobacco material.

Use of a textured sheet of homogenised tobacco material may advantageously facilitate gathering of the sheet of homogenised tobacco material to form the aerosol-generating substrate.

As used herein, the term 'crimped sheet' denotes a sheet having a plurality of substantially parallel ridges or corrugations. Preferably, the substantially parallel ridges or corrugations extend along or parallel to a longitudinal axis of the aerosol-generating article. This advantageously facilitates gathering of the crimped sheet of homogenised tobacco material to form the aerosol-generating article. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article.

As used herein, the term 'aerosol former' is used to describe any suitable known compound or mixture of compounds that, in use, facilitates formation of an aerosol and that is substantially resistant to thermal degradation at the operating temperature of the aerosol-generating article.

Suitable aerosol-formers include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate Preferred aerosol formers are polyhydric alcohols or mixtures thereof, such as propylene glycol, triethylene glycol, 1,3-butanediol and, most preferred, glycerine.

The aerosol-generating substrate may comprise a single aerosol former. Alternatively, the aerosol-generating substrate may comprise a combination of two or more aerosol formers.

The aerosol-generating substrate may have an aerosol former content of greater than 5 percent on a dry weight basis.

The aerosol aerosol-generating substrate may have an aerosol former content of between approximately 5 percent and approximately 30 percent on a dry weight basis.

The aerosol-generating substrate may have an aerosol former content of approximately 20 percent on a dry weight basis.

In a further alternative set of embodiments, the aerosol-generating article may comprise a capsule defining a compartment in which the aerosol-generating substrate is received, wherein the capacitor is provided on an outer surface of the capsule.

Preferably, the capsule comprises a base, a substantially cylindrical wall extending from the base, and an open end opposite the base. The aerosol-generating article further comprises a seal connected to the capsule and extending across the open end to seal the aerosol-generating substrate within the compartment, wherein the capacitor is provided on the base of the capsule.

Providing the capacitor on the base of such a capsule can facilitate reliable and secure contact between the first and second electrodes and corresponding electrical contacts in an aerosol-generating device into which the aerosol-generating article is inserted.

For example, the base is preferably substantially circular, wherein the first electrode overlies at least a portion of the base, wherein the dielectric material overlies a first portion of the first electrode, wherein the second electrode overlies at least a portion of the dielectric material and overlies the centre of the substantially circular base, and wherein the first electrode comprises a second portion that does not underlie either the dielectric material or the second electrode, the second portion being spaced apart from the centre of the substantially circular base. Providing the first electrode with a second portion that does not underlie either the dielectric material or the second electrode may facilitate connection of the first electrode to a corresponding electrical contact of an aerosol-generating device when the aerosol-generating article is combined with the aerosol-generating device to form an aerosol-generating system.

Preferably, the first and second electrodes are configured to facilitate contact between the first and second electrode and corresponding electrical contacts on an aerosol-generating device regardless of the rotational orientation of the substantially circular base when the aerosol-generating article is inserted into the aerosol-generating device. For example, the first and second electrodes may be configured to engage with concentric circular or annular electrical contacts provided in an aerosol-generating device.

Additionally, or alternatively, the first electrode may have a substantially circular shape that concentrically overlies at least a portion of the base, wherein the dielectric material has a substantially circular shape and concentrically overlies the first portion of the first electrode, wherein the second electrode has a substantially circular shape and concentrically overlies at least a portion of the dielectric material, and wherein a diameter of the first electrode is larger than a diameter of the dielectric material and the second electrode so that the second portion of the first electrode has an annular shape provided concentrically on the substantially circular base. Such embodiments may eliminate the need for providing concentric electrical contacts on an aerosol-generating device by providing concentric first and second electrodes that can permit any rotational orientation of the aerosol-generating article with respect to the aerosol-generating device.

In those embodiments in which the aerosol-generating article comprises a capsule defining a compartment in which the aerosol-generating substrate is received, preferably the aerosol-generating substrate comprises tobacco, more preferably at least one of pipe tobacco, cut filler, reconstituted tobacco, homogenised tobacco, and combinations thereof.

The aerosol-generating substrate may comprise an aerosol-former. The aerosol-generating substrate preferably comprises homogenised tobacco material, an aerosol-former and water. Providing homogenised tobacco material may improve aerosol generation, the nicotine content and the flavour profile of the aerosol generated during heating of the aerosol-generating article. Specifically, the process of making homogenised tobacco involves grinding tobacco leaf, which more effectively enables the release of nicotine and flavours upon heating.

The homogenised tobacco material is preferably provided in sheets which are one of folded, crimped, or cut into strips. In a particularly preferred embodiment, the sheets are cut into strips having a width of between about 0.2 millimetres and about 2 millimetres, more preferably between about 0.4 millimetres and about 1.2 millimetres. In one embodiment, the width of the strips is about 0.9 millimetres.

Alternatively, the homogenised tobacco material may be formed into spheres using spheronisation. The mean diameter of the spheres is preferably between about 0.5 millimetres and about 4 millimetres, more preferably between about 0.8 millimetres and about 3 millimetres.

The aerosol-generating substrate preferably comprises: homogenised tobacco material between about 55 percent and about 75 percent by weight; aerosol-former between about 15 percent and about 25 percent by weight; and water between about 10 percent and about 20 percent by weight.

Before measuring the samples of aerosol-generating substrate they are equilibrated for 48 hours at 50 percent relative humidity at 22 degrees Celsius. The Karl Fischer technique is used to determine the water content of the homogenised tobacco material.

The aerosol-generating substrate may further comprise a flavourant between about 0.1 percent and about 10 percent by weight. The flavourant may be any suitable flavourant known in the art, such as menthol.

Sheets of homogenised tobacco material for use in aerosol-generating articles comprising a capsule may be formed by agglomerating particulate tobacco obtained by grinding or otherwise comminuting one or both of tobacco leaf lamina and tobacco leaf stems.

Sheets of homogenised tobacco material for use in aerosol-generating articles comprising a capsule may comprise one or more intrinsic binders that is a tobacco endogenous binder, one or more extrinsic binders that is a tobacco exogenous binder, or a combination thereof to help agglomerate the particulate tobacco. Alternatively, or in addition, sheets of homogenised tobacco material may comprise other additives including, but not limited to, tobacco and non-tobacco fibres, flavourants, fillers, aqueous and non-aqueous solvents and combinations thereof.

Suitable extrinsic binders for inclusion in sheets of homogenised tobacco material for use in aerosol-generating articles comprising a capsule are known in the art and include, but are not limited to: gums such as, for example, guar gum, xanthan gum, arabic gum and locust bean gum; cellulosic binders such as, for example, hydroxypropyl cellulose, carboxymethyl cellulose, hydroxyethyl cellulose, methyl cellulose and ethyl cellulose; polysaccharides such as, for example, starches, organic acids, such as alginic acid, conjugate base salts of organic acids, such as sodium-alginate, agar and 30 pectins; and combinations thereof.

A number of reconstitution processes for producing sheets of homogenised tobacco materials are known in the art. These include, but are not limited to: paper-making processes of the type described in, for example, U.S. Pat. No. 3,860,012; casting or 'cast leaf' processes of the type described in, for example, U.S. Pat. No. 5,724,998; dough reconstitution processes of the type described in, for example, U.S. Pat. No. 3,894,544; and extrusion processes of the type described in, for example, in GB-A-983,928. Typically, the densities of sheets of homogenised tobacco material produced by extrusion processes and dough reconstitution processes are greater than the densities of sheets of homogenised tobacco materials produced by casting processes.

Sheets of homogenised tobacco material for use in aerosol-generating articles comprising a capsule are preferably formed by a casting process of the type generally comprising casting a slurry comprising particulate tobacco and one or more binders onto a conveyor belt or other support surface, drying the cast slurry to form a sheet of homogenised tobacco material and removing the sheet of homogenised tobacco material from the support surface.

The homogenised tobacco sheet material may be produced using different types of tobacco. For example, tobacco sheet material may be formed using tobaccos from a number of different varieties of tobacco, or tobacco from different regions of the tobacco plant, such as leaves or stem. After processing, the sheet has consistent properties and a homogenised flavour. A single sheet of homogenised tobacco material may be produced to have a specific flavour. To produce a product having a different flavour, a different tobacco sheet material needs to be produced. Some flavours that are produced by blending a large number of different shredded tobaccos in a conventional cigarette may be difficult to replicate in a single homogenised tobacco sheet. For example, Virginia tobaccos and Burley tobaccos may need to be processed in different ways to optimise their individual flavours. It may not be possible to replicate a particular blend of Virginia and Burley tobaccos in a single sheet of homogenised tobacco material. As such, the aerosol-generating substrate may comprise a first homogenised tobacco material and a second homogenised tobacco material. By combining two different sheets of tobacco material in a single aerosol-generating substrate, new blends may be created that could not be produced by a single sheet of homogenised tobacco.

The aerosol-former preferably comprises at least one polyhydric alcohol. In a preferred embodiment, the aerosol-former comprises at least one of: triethylene glycol; 1,3-butanediol; propylene glycol; and glycerine.

In any of the embodiments described above, the dielectric material may comprise a paper sheet and the at least one liquid sorbed onto the paper sheet, particularly in those embodiments described above in which the aerosol-generating article comprises a wrapper, wherein at least a portion of the wrapper forms the dielectric material.

The solid components of the paper sheet form the porous substrate material. The liquid sorbed into the porous substrate material may comprise the residual moisture content of the paper after the paper has been formed using a conventional paper-making process, such as a wet-laying process. Additionally, or alternatively, a liquid may be added to the paper after the paper has been formed. The liquid may comprise water.

According to a second aspect of the present invention there is provided an aerosol-generating article comprising an aerosol-generating substrate and a capacitor. The capacitor comprises a first electrode, a second electrode, and a dielectric material positioned between the first electrode and the second electrode. The dielectric material comprises a porous substrate material and a liquid sorbed into the porous substrate material. The aerosol-generating substrate may comprise a non-tobacco material. In preferred embodiments, the aerosol-generating substrate comprises tobacco. The aerosol-generating article may further comprise any of the optional and preferred features described herein with respect to the first aspect of the present invention.

The present invention also extends to aerosol-generating systems comprise an aerosol-generating device in combination with an aerosol-generating article in accordance with the first aspect of the present invention or the second aspect of the present invention.

Therefore, according to a third aspect of the present invention there is provided an aerosol-generating system comprising an aerosol-generating device and an aerosol-generating article according to the first aspect of the present invention or the second aspect of the present invention, in accordance with any of the embodiments described above. The aerosol-generating device comprises a power supply, at least one heater, and a cavity for receiving the aerosol-generating article. The aerosol-generating device further comprises a first electrical contact for contacting the first electrode of the capacitor when the aerosol-generating article is received within the cavity, and a second electrical contact for contacting the second electrode of the capacitor when the aerosol-generating article is received within the cavity. The aerosol-generating device also comprises a controller for controlling a supply of power from the power supply to the at least one heater for heating the aerosol-generating substrate and the dielectric material and for controlling a supply of power from the power supply to the capacitor. The controller is configured to measure the capacitance of the capacitor via the first and second electrical contacts and the controller is configured to terminate the supply of power from the power supply to the at least one heater when the measured capacitance exceeds a predetermined threshold.

In some embodiments, and particularly those embodiments in which the aerosol-generating substrate comprises a plug or a rod of a tobacco material, the at least one heater preferably comprises an elongate heater configured for insertion into the aerosol-generating substrate when the aerosol-generating article is received within the cavity. The elongate heater may have any suitable shape to facilitate insertion into the aerosol-generating substrate. For example, the elongate heater may be a heater blade.

Additionally, or alternatively, the at least one heater may comprise a heater positioned adjacent to an outer surface of the aerosol-generating article when the aerosol-generating article is received within the cavity. Such embodiments may be particularly suited to those embodiments in which the aerosol-generating article comprises a capsule defining a compartment in which the aerosol-generating substrate is received. For example, the at least one heater may comprise a substantially annular heater configured to surround at least a portion of the aerosol-generating article when the aerosol-generating article is received within the cavity. Additionally, or alternatively, the at least one heater may comprise a substantially planar heater positioned adjacent to an end of the aerosol-generating article when the aerosol-generating article is received within the cavity.

In any of the embodiments described above, the at least one heater preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Examples of suitable composite heater elements are disclosed in U.S. Pat. No. 5,498,855, WO-A-03/095688 and U.S. Pat. No. 5,514,630.

In any of the embodiments described above, the first and second electrical contacts may be provided on an end wall of the cavity. In some embodiments, the first and second electrical contacts may be concentrically provided on the end wall to facilitate contact with the first and second electrodes regardless of the rotational orientation of the aerosol-generating article. For example, the first electrical contact may be substantially annular and the second electrical contact may be substantially circular or substantially annular, wherein the second electrical contact is provided concentrically within the first electrical contact, and wherein the first and second electrical contacts are spaced apart.

Alternatively, the first and second electrical contacts may be provided on an inner surface of a longitudinally extending wall of the cavity. In some embodiments, each of the first and second electrical contacts may be annular and extend around the circumference of the cavity to facilitate contact with the first and second electrodes respectively, regardless of the rotational orientation of the aerosol-generating article.

FIG. 1 shows an aerosol-generating article 10 comprising an aerosol-generating substrate 12, a hollow acetate tube 14, a polymeric filter 16, a mouthpiece 18 and an outer wrapper 20. The aerosol-generating substrate 12 comprises a plug of tobacco and the mouthpiece 18 comprises a plug of cellulose acetate fibres.

The aerosol-generating article 10 further comprises a capacitor 22 provided on an outer surface of the outer wrapper 20, adjacent to the aerosol-generating substrate 12. The capacitor 22 comprises a first electrode 24 secured to the outer wrapper 20, a dielectric material 26 overlying a first portion of the first electrode 24, and a second electrode 28 overlying the dielectric material. The dielectric material 26 comprises a sheet of paper and a liquid sorbed into the sheet of paper. The first electrode 24 comprises a second portion 29 that does not underlie the dielectric material 26 or the second electrode 28, the second portion 29 facilitating connection of the first electrode 24 to an electrical contact when the aerosol-generating article 10 is received within an aerosol-generating device, as described in detail with reference to FIG. 2.

The thickness of the capacitor 22 has been exaggerated in FIG. 1 (and FIGS. 2 to 11) to clearly show the first electrode 24, the dielectric material 26 and the second electrode 28.

Figure 2:
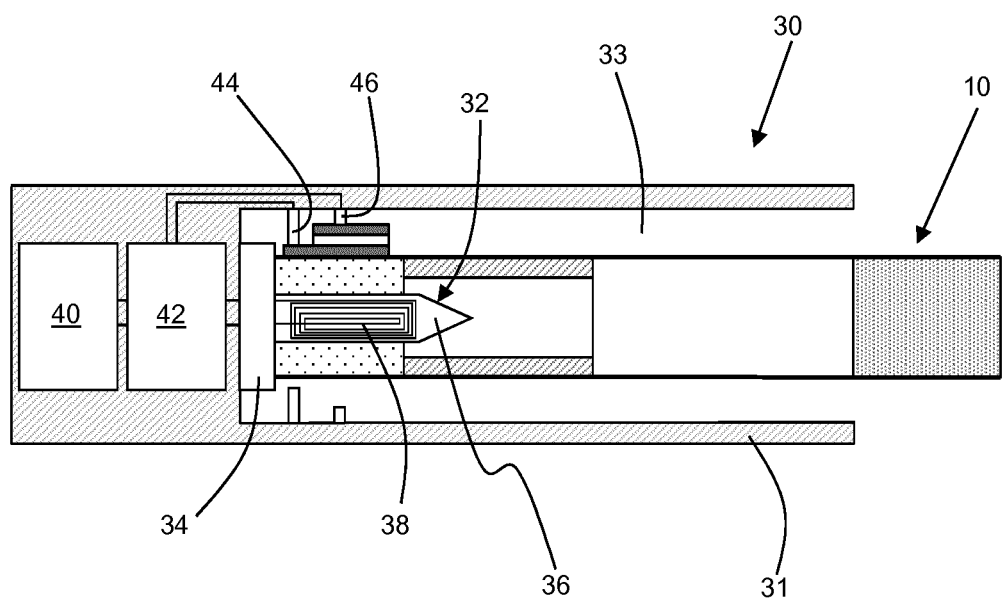
FIG. 2 shows the aerosol-generating article of FIG. 1 inserted into an aerosol-generating device to form an aerosol-generating system in accordance with the present invention.

FIG. 2 shows the aerosol-forming article 10 inserted into an electrically heated aerosol-generating device 30. The device 30 comprises a housing 31 defining a cavity 33 for receiving the aerosol-generating article 10. The device 30 includes a heater 32 comprising a base portion 34 and a heater blade 36 that penetrates the aerosol-generating substrate 12 when the aerosol-generating article 10 is inserted into the cavity 33. The heater blade 36 comprises a resistive heating coil 38 for resistively heating the upstream end of the aerosol-generating article 10. A controller 42 controls the operation of the device 30, including the supply of electrical current from a battery 40 to the resistive heating coil 38 of the heater blade 36.

The aerosol-generating device 30 further comprises a first electrical contact 44 and a second electrical contact 46 arranged to contact the first electrode 24 and the second electrode 28 respectively, when the aerosol-generating article 10 is fully inserted into the cavity 33. The first and second electrical contacts 44, 46 are annular so that they contact the first and second electrodes 24, 28 regardless of the rotational orientation of the aerosol-generating article 10 within the cavity 33.

During use, the controller 42 supplies electrical current from the battery 40 to the resistive heating coil 38 to heat the aerosol-generating substrate 12 and the capacitor 22. During the heating cycle, at least some of the liquid sorbed into the paper sheet of the dielectric material 26 is evaporated, resulting in a change in the capacitance between the first electrode 24 and the second electrode 28, which is measured by the controller 42 via the first and second electrical contacts 44, 46. When the measured capacitance reaches a predetermined level indicative of a significant depletion of volatile compounds from the aerosol-generating substrate 12, the controller 42 terminates the supply of electrical current from the battery 40 to the resistive heating coil 38 to prevent further heating of the aerosol-generating substrate 12.

FIGS. 3 to 6 illustrate alternative embodiments of the aerosol-generating article 10, each comprising a different configuration of the capacitor. Like reference numerals are used to designate like parts.

Figure 3:
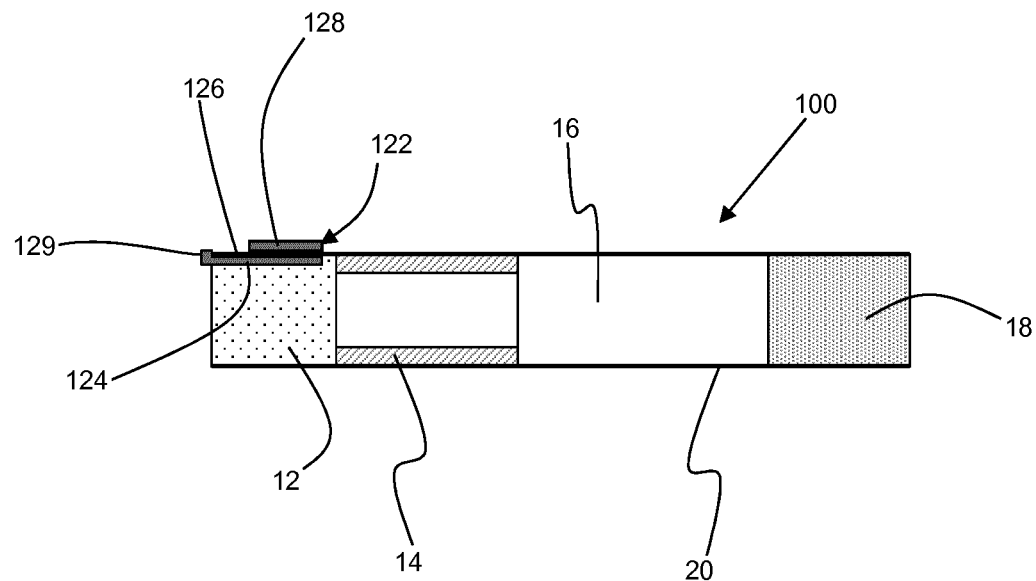
FIGS. 3 to 6 show alternative embodiments of the aerosol-generating article of FIG. 1.

The aerosol-generating article 100 shown in FIG. 3 includes a capacitor 122 comprising a first electrode 124 provided on an inner surface of the outer wrapper 20 and a second electrode 128 provided on the outer surface of the outer wrapper 20, the second electrode 128 overlying a first portion of the first electrode 124. In this embodiment, the dielectric material 126 is formed by the portion of the outer wrapper 20 positioned between the first and second electrodes 124, 128. A second portion 129 of the first electrode 124 protrudes from the upstream end of the aerosol-generating article 100 to facilitate connection of the first electrode 124 to an electrical contact in an aerosol-generating device.

Figure 4:
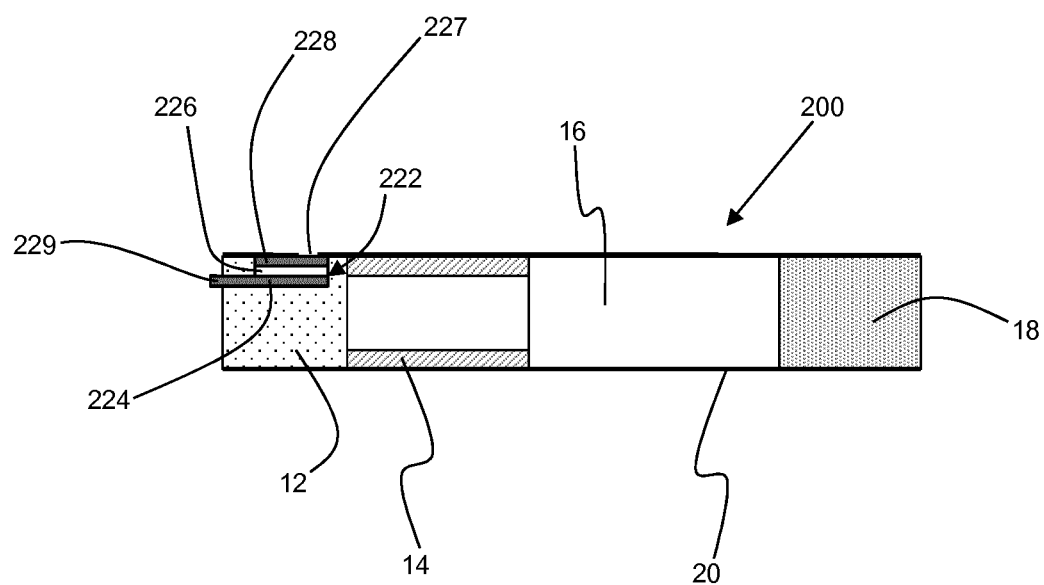

The aerosol-generating article 200 shown in FIG. 4 includes a capacitor 222 comprising a first electrode 224 provided within the aerosol-generating substrate 12, a dielectric material 226 overlying a first portion of the first electrode 224, and a second electrode 228 overlying the dielectric material 226 and underlying the outer wrapper 20. An aperture 227 provided in the outer wrapper 20 facilitates connection of the second electrode 228 to an electrical contact in an aerosol-generating device. A second portion 229 of the first electrode 224 protrudes from the upstream end of the aerosol-generating article 200 to facilitate connection of the first electrode 224 to an electrical contact in an aerosol-generating device.

Figure 5:
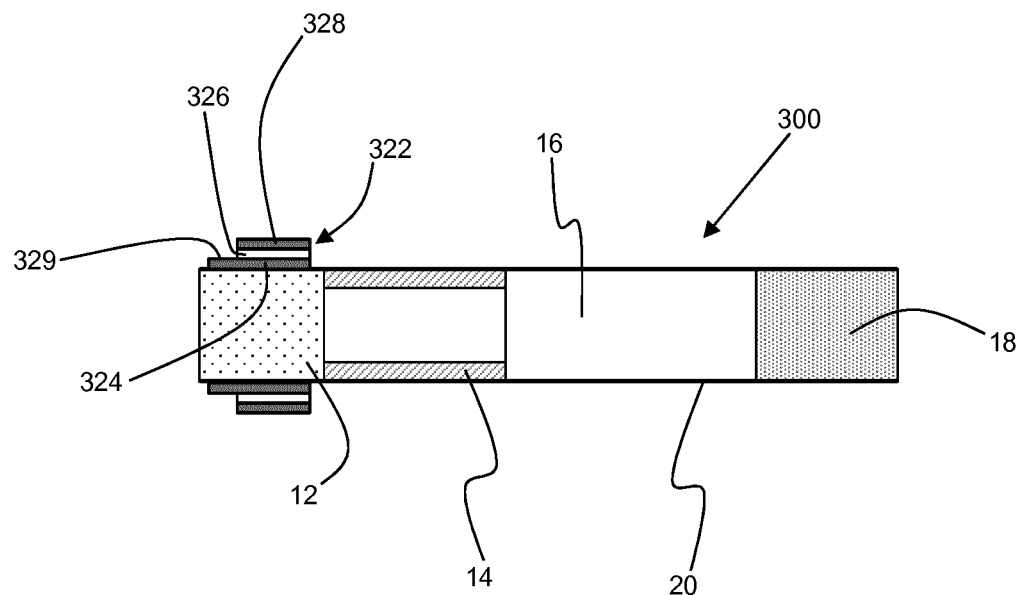

The aerosol-generating article 300 shown in FIG. 5 includes a capacitor 322 comprising an annular first electrode 324 provided on the outer surface of the outer wrapper 20, a dielectric material 326 overlying a first portion of the first electrode 324, and a second electrode 328 overlying the dielectric material 326. A second portion 329 of the first electrode 324 does not underlie the dielectric material 326 or the second electrode 328 to facilitate connection of the first electrode 324 to an electrical contact in an aerosol-generating device. Using annular first and second electrodes 324, 328 can eliminate the need to provide annular electrical contacts in the aerosol-generating device while still permitting the insertion of the aerosol-generating article 300 into the aerosol-generating device in any rotational orientation.

Figure 6:
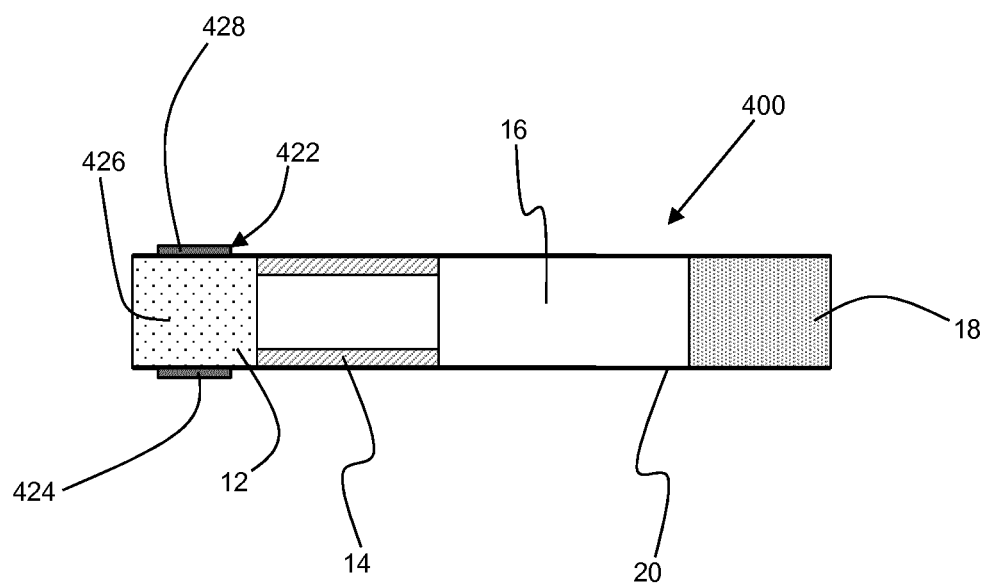

The aerosol-generating article 400 shown in FIG. 6 includes a capacitor 422 comprising a first electrode 424 provided on the outer surface of the outer wrapper 20 and a second electrode 428 provided on the outer surface of the outer wrapper 20 on an opposite side of the aerosol-generating article 400. In this embodiment, the dielectric material 426 is formed by the portion of the aerosol-generating substrate 12 positioned between the first and second electrodes 424, 428.

Figure 7:
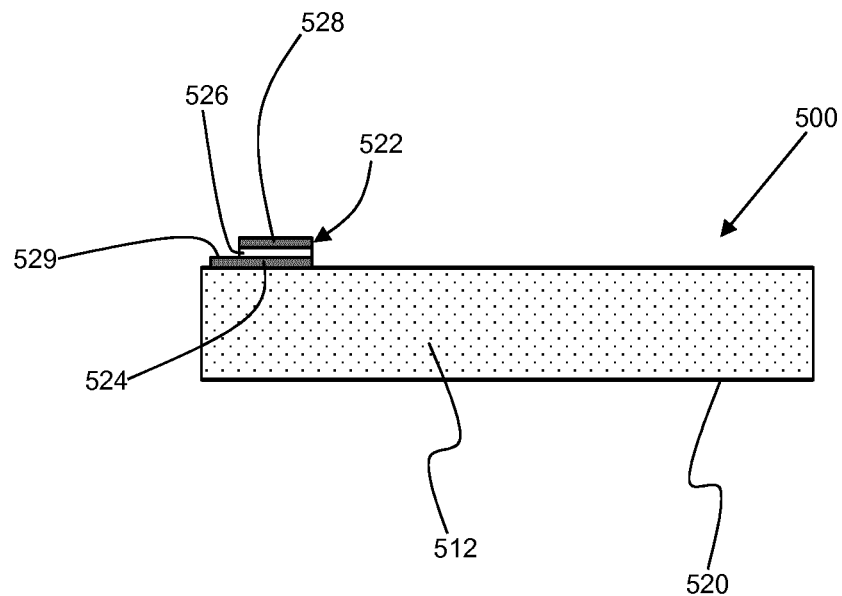
FIG. 7 shows an alternative aerosol-generating article in accordance with the present invention.

FIG. 7 shows an alternative aerosol-generating article 500 comprising an aerosol-generating substrate 512 wrapped in an outer wrapper 520. The aerosol-generating substrate 512 is a tobacco rod.

The aerosol-generating article 500 further comprises a capacitor 522 provided on an outer surface of the outer wrapper 520. The capacitor 522 comprises a first electrode 524 secured to the outer wrapper 520, a dielectric material 526 overlying a first portion of the first electrode 524, and a second electrode 528 overlying the dielectric material. The dielectric material 526 comprises a sheet of paper and a liquid sorbed into the sheet of paper. The first electrode 524 comprises a second portion 529 that does not underlie the dielectric material 526 or the second electrode 528, the second portion 529 facilitating connection of the first electrode 524 to an electrical contact when the aerosol-generating article 500 is received within an aerosol-generating device, as described in detail with reference to FIG. 8.

Figure 8:
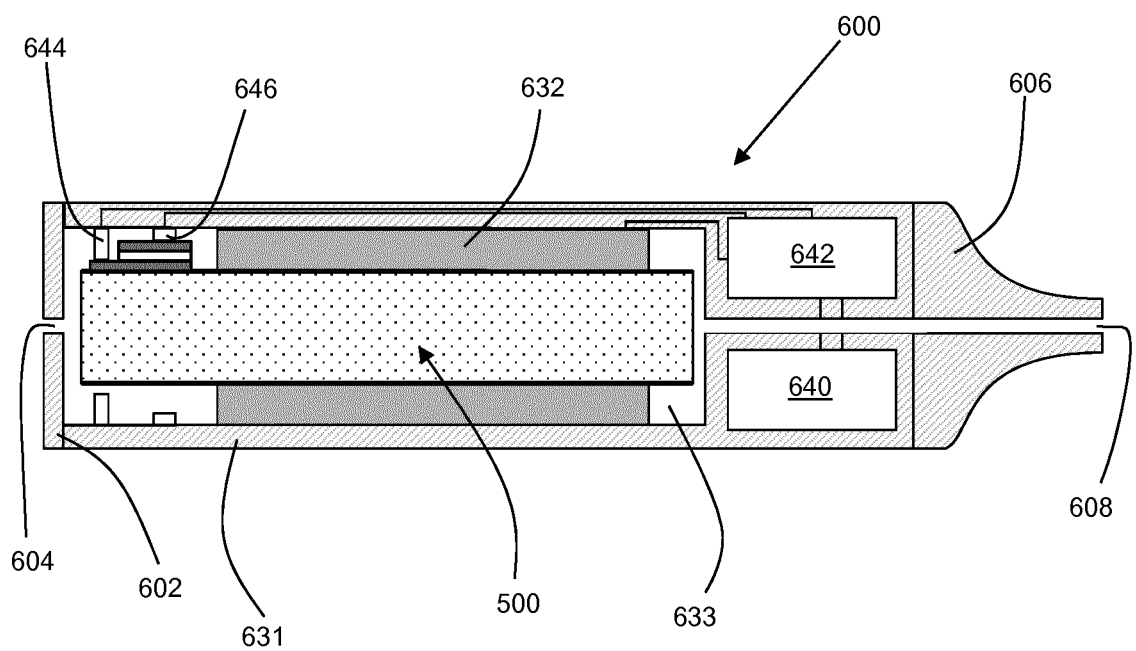
FIG. 8 shows the aerosol-generating article of FIG. 7 inserted into an aerosol-generating device to form an alternative aerosol-generating system in accordance with the present invention.

FIG. 8 shows the aerosol-forming article 500 inserted into an electrically heated aerosol-generating device 600. The device 600 comprises a housing 631 defining a cavity 633 for receiving the aerosol-generating article 500. A removable end cap 602 can be removed to allow insertion of the aerosol-generating article 500 into the cavity 633, the removable end cap 602 comprising an air inlet 604 to admit air into the cavity 633 during use. The device 600 includes an annular heater 632 into which the aerosol-generating article 500 is received. A controller 642 controls the operation of the device 600, including the supply of electrical current from a battery 640 to the annular heater 632. A mouthpiece 606 at a downstream end of the device 600 includes an air outlet 608 to allow a consumer to draw air through the aerosol-generating article 500 and the device 600 during use.

The aerosol-generating device 600 further comprises a first electrical contact 644 and a second electrical contact 646 arranged to contact the first electrode 524 and the second electrode 528 respectively, when the aerosol-generating article 500 is fully inserted into the cavity 633. The first and second electrical contacts 644, 646 are annular so that they contact the first and second electrodes 524, 528 regardless of the rotational orientation of the aerosol-generating article 500 within the cavity 633.

During use, the controller 642 supplies electrical current from the battery 640 to the annular heater 632 to heat the aerosol-generating substrate 512 and the capacitor 522. During the heating cycle, at least some of the liquid sorbed into the paper sheet of the dielectric material 526 is evaporated, resulting in a change in the capacitance between the first electrode 524 and the second electrode 528, which is measured by the controller 642 via the first and second electrical contacts 644, 646. When the measured capacitance reaches a predetermined level indicative of a significant depletion of volatile compounds from the aerosol-generating substrate 512, the controller 642 terminates the supply of electrical current from the battery 640 to the annular heater 632 to prevent further heating of the aerosol-generating substrate 512.

The skilled person will appreciate that any of the alternative capacitor arrangements described with reference to FIGS. 3 to 6 can be applied equally to the aerosol-generating article 500 shown in FIG. 7.

Figure 9:
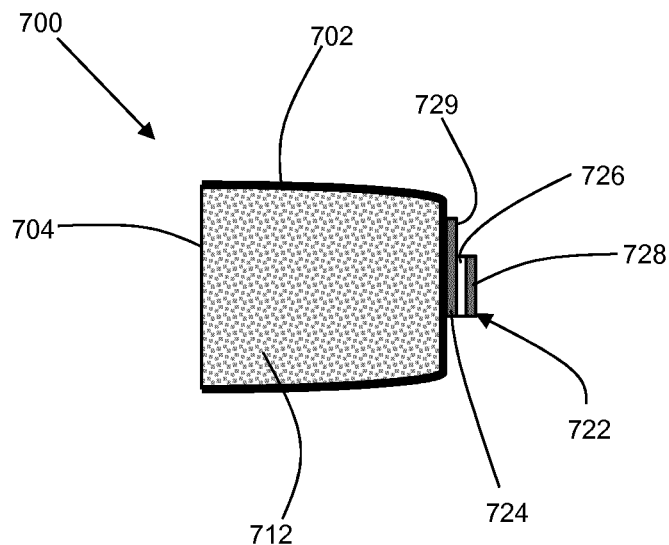
FIG. 9 shows a further alternative aerosol-generating article in accordance with the present invention.

FIG. 9 shows a further alternative aerosol-generating article 700 comprising a capsule 702 defining a compartment in which an aerosol-generating substrate 712 is provided. The aerosol-generating substrate 712 comprises loose tobacco. The capsule 712 comprises a base on which a capacitor 722 is provided, and a seal 704 connected to the capsule 702 to seal an open end of the compartment opposite the base.

The capacitor 722 comprises a first electrode 724 secured to the base of the capsule 702, a dielectric material 726 overlying a first portion of the first electrode 724, and a second electrode 728 overlying the dielectric material. The dielectric material 726 comprises a sheet of paper and a liquid sorbed into the sheet of paper. The first electrode 724 comprises a second portion 729 that does not underlie the dielectric material 726 or the second electrode 728, the second portion 729 facilitating connection of the first electrode 724 to an electrical contact when the aerosol-generating article 700 is received within an aerosol-generating device, as described in detail with reference to FIG. 10.

Figure 10:
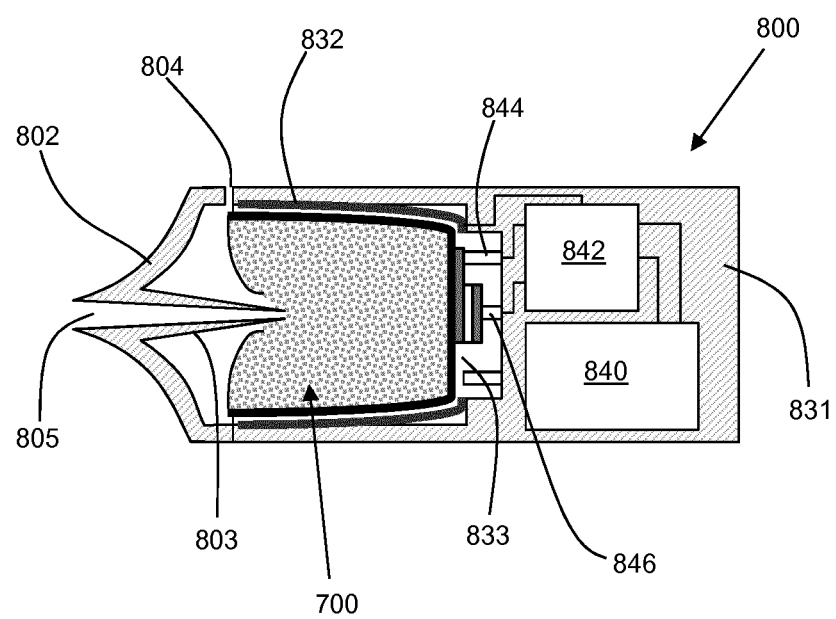
FIG. 10 shows the aerosol-generating article of FIG. 9 inserted into an aerosol-generating device to form a further alternative aerosol-generating system in accordance with the present invention.

FIG. 10 shows the aerosol-forming article 700 inserted into an electrically heated aerosol-generating device 800. The device 800 comprises a housing 831 defining a cavity 833 for receiving the aerosol-generating article 700. A removable mouthpiece 802 can be removed to allow insertion of the aerosol-generating article 700 into the cavity 833, the removable mouthpiece 802 comprising a piercing element 803 for breaking the seal 704 on the aerosol-generating article 700 when the removable mouthpiece 802 is reattached to the housing 831. The removable mouthpiece 802 further comprises an air inlet 804 for admitting air into the cavity 833 and an air outlet 805 extending through the piercing element 803 to allow a consumer to draw air out of the cavity 833 during use.

The device 800 includes an annular heater 832 into which the aerosol-generating article 700 is received. A controller 842 controls the operation of the device 800, including the supply of electrical current from a battery 840 to the annular heater 832.

The aerosol-generating device 800 further comprises a first electrical contact 844 and a second electrical contact 846 arranged to contact the first electrode 724 and the second electrode 728 respectively, when the aerosol-generating article 700 is fully inserted into the cavity 833. The first electrical contact 844 is annular so that it contacts the first electrode 724 regardless of the rotational orientation of the aerosol-generating article 700 within the cavity 833.

During use, the controller 842 supplies electrical current from the battery 840 to the annular heater 832 to heat the aerosol-generating substrate 712 and the capacitor 722. During the heating cycle, at least some of the liquid sorbed into the paper sheet of the dielectric material 726 is evaporated, resulting in a change in the capacitance between the first electrode 724 and the second electrode 728, which is measured by the controller 842 via the first and second electrical contacts 844, 846. When the measured capacitance reaches a predetermined level indicative of a significant depletion of volatile compounds from the aerosol-generating substrate 712, the controller 842 terminates the supply of electrical current from the battery 840 to the annular heater 832 to prevent further heating of the aerosol-generating substrate 712.

Figure 11:
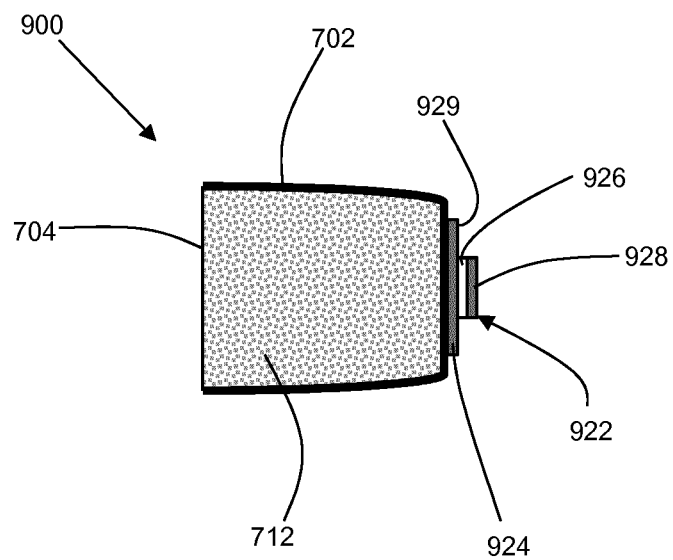
FIG. 11 shows an alternative embodiment of the aerosol-generating article of FIG. 9.

FIG. 11 illustrates and alternative embodiment of the aerosol-generating article 700, wherein like reference numerals are used to designate like parts.

The aerosol-generating article 900 shown in FIG. 11 includes a capacitor 922 comprising a first electrode 924, a dielectric material 926 and a second electrode 928 all provided concentrically on the base of the capsule 702. The first electrode 924 has a larger diameter than the dielectric material 926 and the second electrode 928 so that the first electrode comprises an annular second portion 929 to facilitate connection of the first electrode 924 to an electric contact in an aerosol-generating device. Forming an annular second portion 929 of the first electrode 924 can eliminate the need to provide annular electrical contacts in the aerosol-generating device while still permitting the insertion of the aerosol-generating article 900 into the aerosol-generating device in any rotational orientation.

The invention claimed is:

1. An aerosol-generating article, comprising:
an aerosol-generating substrate comprising tobacco; and
a capacitor comprising a first electrode, a second electrode, and a dielectric material disposed between the first electrode and the second electrode,
wherein the dielectric material comprises a porous substrate material and a liquid sorbed into the porous substrate material.

2. The aerosol-generating article according to claim 1, further comprising a wrapper wrapped around the aerosol-generating substrate,
wherein the capacitor is provided on an outer surface of the wrapper.

3. The aerosol-generating article according to claim 2, wherein the first electrode overlies at least a portion of the wrapper,
wherein the dielectric material overlies a first portion of the first electrode,
wherein the second electrode overlies at least a portion of the dielectric material, and
wherein the first electrode comprises a second portion that does not underlie either the dielectric material or the second electrode.

4. The aerosol-generating article according to claim 1, further comprising a wrapper wrapped around the aerosol-generating substrate,
wherein the first electrode underlies at least a portion of the wrapper,
wherein the second electrode overlies at least a portion of the wrapper, and wherein the portion of the wrapper disposed between the first electrode and the second electrode forms the dielectric material.

5. The aerosol-generating article according to claim 1, further comprising a wrapper wrapped around the aerosol-generating substrate,
wherein the capacitor is disposed between the wrapper and the aerosol-generating substrate.

6. The aerosol-generating article according to claim 1, wherein the aerosol-generating substrate has a substantially cylindrical shape, and
wherein the capacitor has a substantially annular shape and circumscribes at least a portion of the aerosol-generating substrate.

7. The aerosol-generating article according to claim 1, further comprising a capsule defining a compartment in which the aerosol-generating substrate is received,
wherein the capacitor is provided on an outer surface of the capsule.

8. The aerosol-generating article according to claim 7, wherein the capsule comprises a base, a substantially cylindrical wall extending from the base, and an open end opposite the base,
the aerosol-generating article further comprising a seal connected to the capsule and extending across the open end to seal the aerosol-generating substrate within the compartment, and
wherein the capacitor is disposed on the base of the capsule.

9. The aerosol-generating article according to claim 8, wherein the base is substantially circular,
wherein the first electrode overlies at least a portion of the base,
wherein the dielectric material overlies a first portion of the first electrode,
wherein the second electrode overlies at least a portion of the dielectric material and overlies a center of the substantially circular base, and
wherein the first electrode comprises a second portion that does not underlie either the dielectric material or the second electrode, the second portion being spaced apart from the center of the substantially circular base.

10. The aerosol-generating article according to claim 9, wherein the first electrode has a substantially circular shape and concentrically overlies at least a portion of the base,
wherein the dielectric material has a substantially circular shape and concentrically overlies the first portion of the first electrode,
wherein the second electrode has a substantially circular shape and concentrically overlies at least a portion of the dielectric material, and
wherein a diameter of the first electrode is larger than a diameter of the dielectric material and the second electrode, such that the second portion of the first electrode has an annular shape provided concentrically on the substantially circular base.

11. The aerosol-generating article according to claim 1, wherein the dielectric material comprises a paper sheet and the at least one liquid sorbed onto the paper sheet.

12. The aerosol-generating article according to claim 1, wherein at least a portion of the aerosol-generating substrate is disposed between the first electrode and the second electrode such that the portion of the aerosol-generating substrate disposed between the first electrode and the second electrode forms the dielectric material.

13. The aerosol-generating article according to claim 1, wherein the aerosol-generating substrate is non-liquid at room temperature.

14. An aerosol-generating system, comprising:
an aerosol-generating article according to claim 1; and
an aerosol-generating device comprising:
   a power supply;
   at least one heater;
   a cavity configured to receive the aerosol-generating article;
   a first electrical contact configured to contact the first electrode of the capacitor when the aerosol-generating article is received within the cavity;
   a second electrical contact configured to contact the second electrode of the capacitor when the aerosol-generating article is received within the cavity; and
   a controller configured to control a supply of power from the power supply to the at least one heater for heating the aerosol-generating substrate and the dielectric material, and to control a supply of power from the power supply to the capacitor,
wherein the controller is further configured to measure a capacitance of the capacitor via the first and second electrical contacts, and to terminate the supply of power from the power supply to the at least one heater when a measured capacitance exceeds a predetermined threshold.

* * * * *